United States Patent [19]

Holtkamp

[11] Patent Number: Plant 5,725

[45] Date of Patent: Apr. 22, 1986

[54] AFRICAN VIOLET PLANT NAMED ARKANSAS

[75] Inventor: Reinhold Holtkamp, Isselburg, Fed. Rep. of Germany

[73] Assignee: "Optimara", Fed. Rep. of Germany

[21] Appl. No.: 477,721

[22] Filed: Mar. 22, 1983

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

An African violet plant named Arkansas having exceptionally long lasting and non-dropping purple flowers, with 7–10 more flowers being carried on upright, wire-like flower stems curving to the center, vigorous growth habit, serrated dark green leaves with margins slightly waved and which are symmetrical out of the center of a plant, and by its full bouquet and profuse flowering.

1 Drawing Figure

The present invention comprises a new and distinct cultivar of African violet plant, botanically known as *Saintpaulia ionantha,* and hereinafter referred to by the cultivar name Arkansas.

The new cultivar was referred to during the breeding and selection process by the designation B 15/8, and is a product of a planned breeding program.

The new cultivar was originated from a cross made in a controlled breeding program in Isselburg, West Germany. The female, or seed parent was a cultivar designated XX 4256 blue single. The male, or pollen parent was a cultivar designated XX 4158 purplish red.

The new cultivar Arkansas was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Arkansas has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Arkansas, which in combination distinguish this African violet as a new and distinct cultivar:

(1) Very symmetrical leaf formation out of the center.

(2) Upright, wire-like flower stems curing to the center.

(3) Well pronounced serrated dark green leaves having dark purplish undersides.

(4) Leaf margin slightly waved.

(5) Vigorous grower.

(6) 7–10 and more flowers per stem.

(7) Flowers are exceptionally long lasting and non-dropping.

The new cultivar is very unique with regard to overall characteristics, but is similar in color to the cultivar North Carolina, disclosed in my U.S. Plant Pat. No. 4,415.

The accompanying photographic drawing shows a typical specimen plant of the new cultivar. The colors appearing in the photograph are as true as possible with color illustrations of this type.

In the following description, color references are made to The Horticultural Colour Chart (H.C.C.) issued by Wilson Colour Ltd., except where general colors of ordinary significance are referred to. Color values were taken under natural light conditions approximately mid-day in Nashville, Tenn.

Botanical Classification: *Saintpaulia ionantha,* Ramat. cv Arkansas.

Parentage:

*Male parent.*—XX 4158 purplish red.

*Female parent.*—XX 4256 blue single.

Propagation: The new cultivar holds its distinguishing characteristics through successive propagations by leaf cuttings and by division of shoots.

Plant: From 7 cm. to 12 cm. tall when grown in pots, and approximately 25 cm. in diameter when fully grown.

Leaves:

*General form.*—Round to broadly ovate.

*Diameter.*—50–60 mm.

*Texture.*—Soft.

*Aspect.*—Shiny, dark green, hairy.

*Veins.*—Well pronounced.

*Color (upperside).*—Ivy green 0001060.

*Color (underside).*—Dark purplish maroon 1030/2.

*Petiole.*—Maroon 1030/2.

Flowers:

*Buds.*—Bell shape; 9–12 and more.

*Sepals.*—Spear shape. Color: Maroon, hairy. Aspect: Flat funnel shape. Peduncle: Maroon, strong, upright.

*Individual flowers.*—Size: 30–35 mm. Color: Upperside: Doge purple 732. Underside: Imperial purple 33/1. Borne: Upright on short pedicel. Shape: Violet shape, slightly frilled, normal flower has 5 petals, with flowers occasionally having additional petals. Corolla: Compact flower bouquet. Flowering time: 9–11 weeks after potting.

Reproductive organs:

*Anthers.*—Two compounds of four cells.

*Styles.*—Same color as petals, only tip is white.

*Pollen color.*—Canary yellow 2.

Roots: Normal developed.

Disease resistance: Good as known to date.

General observations:

Arkansas is one of the most long lasting varieties developed to date. The flowers are carried on upright wire-like peduncles and pedicels. The flowers are slightly frilled and undulated. The first flash of flowers form a full bouquet, and the second flowering after disbudding is twice as heavy.

I claim:

1. An African violet plant named Arkansas, as described and illustrated, and particularly characterized by its exceptionally long lasting and non-dropping purple flowers, with 7–10 more flowers being carried on upright, wire-like flower stems curving to the center, vigorous growth habit, serrated dark green leaves with margins slightly waved and which are symmetrical out of the center of a plant, and by its full bouquet and profuse flowering.

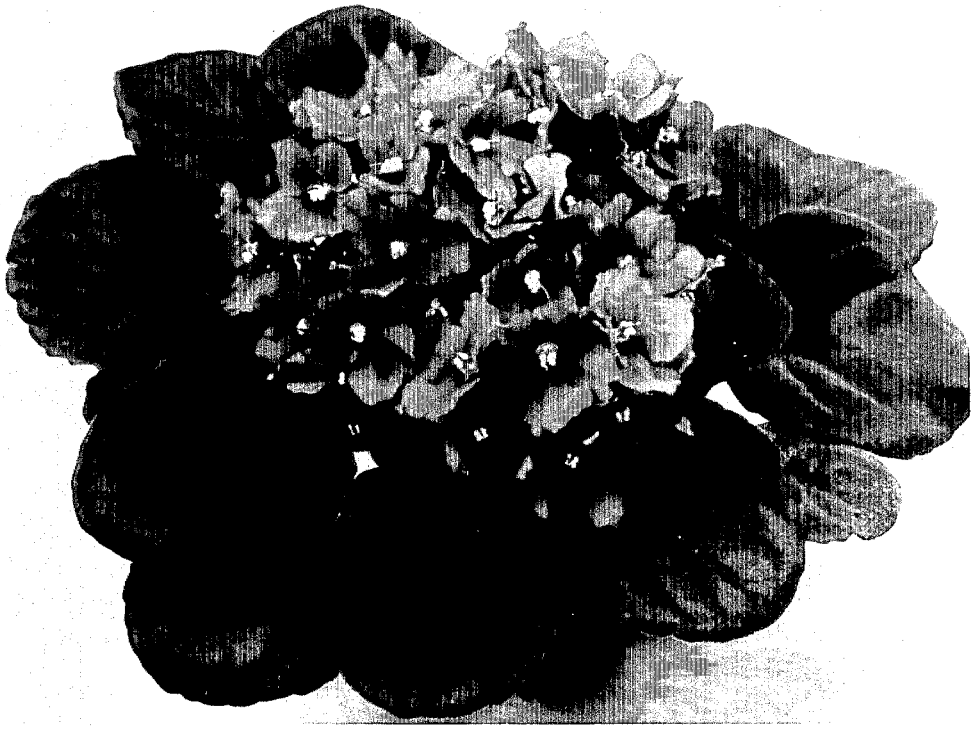

* * * * *